United States Patent
Kim et al.

(10) Patent No.: US 9,610,065 B2
(45) Date of Patent: Apr. 4, 2017

(54) PROBE CONTROL METHOD AND APPARATUS

(71) Applicant: SAMSUNG MEDISON CO., LTD., Gangwon-Do (KR)

(72) Inventors: Hyoung-Jin Kim, Gangwon-Do (KR); Nam-Woong Kim, Gangwon-Do (KR); Dong-Gyu Hyun, Gangwon-Do (KR)

(73) Assignee: Samsung Medison Co., Ltd., Hongcheon-gun, Gangwon-do (KR)

(*) Notice: Subject to any disclaimer, the term of this patent is extended or adjusted under 35 U.S.C. 154(b) by 222 days.

(21) Appl. No.: 14/457,013

(22) Filed: Aug. 11, 2014

(65) Prior Publication Data

US 2015/0045673 A1 Feb. 12, 2015

(30) Foreign Application Priority Data

Aug. 12, 2013 (KR) .................. 10-2013-0095609

(51) Int. Cl.
*A61B 8/14* (2006.01)
*A61B 8/00* (2006.01)
*A61B 8/08* (2006.01)

(52) U.S. Cl.
CPC .............. *A61B 8/54* (2013.01); *A61B 8/4438* (2013.01); *A61B 8/4444* (2013.01); *A61B 8/5207* (2013.01); *A61B 8/4209* (2013.01); *A61B 8/4405* (2013.01); *A61B 8/4477* (2013.01); *A61B 8/488* (2013.01)

(58) Field of Classification Search
CPC ....... A61B 8/54; A61B 8/4438; A61B 8/5207; A61B 8/4444; A61B 8/4209; A61B 8/4477; A61B 8/4405; A61B 8/488

USPC .................................. 600/437–469
See application file for complete search history.

(56) References Cited

U.S. PATENT DOCUMENTS

| 5,505,203 A * | 4/1996 | Deitrich ............ A61B 8/00 600/437 |
| 5,552,645 A * | 9/1996 | Weng ............ A61B 5/0002 307/112 |
| 6,733,450 B1 * | 5/2004 | Alexandrov ............ A61N 7/00 600/439 |
| 7,393,326 B2 * | 7/2008 | Bindefeld ............ A61B 7/02 181/131 |

(Continued)

FOREIGN PATENT DOCUMENTS

| EP | 1 676 530 A1 | 7/2006 |
| JP | 2000-014670 A | 1/2000 |

(Continued)

OTHER PUBLICATIONS

Korean Office Action dated Jun. 16, 2015 issued in corresponding Korean Patent Application No. 10-2015-0069093, with English translation.

(Continued)

*Primary Examiner* — Sanjay Cattungal
(74) *Attorney, Agent, or Firm* — McDermott Will & Emery LLP (57) ABSTRACT

Disclosed are a probe control method and apparatus and an ultrasound system which apply a mounting signal used to sense a mounting status of a probe, detect the mounting signal transferred through a cable, and automatically activate/deactivate the probe according to a change in a sensed mounting status.

23 Claims, 9 Drawing Sheets

(56) References Cited

U.S. PATENT DOCUMENTS

| | | | |
|---|---|---|---|
| 2002/0103436 A1* | 8/2002 | Njemanze | A61B 8/06 600/453 |
| 2005/0038339 A1* | 2/2005 | Chauhan | A61B 34/32 600/439 |
| 2006/0173346 A1 | 8/2006 | Lee | |
| 2007/0232907 A1* | 10/2007 | Pelissier | A61B 8/00 600/437 |
| 2007/0293763 A1 | 12/2007 | Matsumura | |
| 2009/0227873 A1* | 9/2009 | Mesaros | A61B 8/462 600/459 |
| 2013/0158397 A1* | 6/2013 | K | G06F 19/322 600/437 |
| 2013/0310691 A1* | 11/2013 | Furman | A61B 8/06 600/447 |
| 2014/0107487 A1 | 4/2014 | Kim et al. | |
| 2015/0045673 A1* | 2/2015 | Kim | A61B 8/4438 600/459 |
| 2016/0106396 A1* | 4/2016 | Jin | A61B 8/54 600/437 |
| 2016/0109409 A1* | 4/2016 | Bentouhami | G01N 29/30 73/620 |

FOREIGN PATENT DOCUMENTS

| | | |
|---|---|---|
| JP | 2000-107176 A | 4/2000 |
| JP | 2005-192868 A | 7/2005 |
| JP | 2007-101432 A | 4/2007 |
| JP | 2008-253500 A | 10/2008 |
| KR | 10-2006-0075733 A | 7/2006 |
| KR | 10-1038410 B1 | 6/2011 |
| KR | 10-2013-0081820 A | 7/2013 |
| KR | 10-2013-0095609 A | 8/2013 |
| KR | 2014-0046754 A | 4/2014 |

OTHER PUBLICATIONS

Notice of Non-Final Rejection dated Nov. 27, 2014 issued in Korean Patent Application No. 10-2013-0095609 (English translation).
Extended Search Report dated Jan. 29, 2015 issued in European Patent Application No. 14172055.7.
Notice of Final Rejection dated Feb. 26, 2015 issued in Korean Patent Application No. 10-2013-0095609, with English translation.
Notice of Final Rejection dated Apr. 16, 2015 issued in Korean Patent Application No. 10-2013-0095609, with English translation.
Notice of Allowance issued in corresponding Korean Patent Application No. 10-2015-0069093, mailed on Jan. 9, 2016; with English translation.

* cited by examiner

PROBE CONTROL METHOD AND APPARATUS

RELATED APPLICATIONS

This application claims the benefit of Korean Patent Application No. 10-2013-0095609, filed on Aug. 12, 2013, in the Korean Intellectual Property Office, the disclosure of which is incorporated herein in its entirety by reference.

BACKGROUND

1. Field

One or more embodiments of the present invention relate to a probe control method and apparatus for actively controlling a probe included in an ultrasound diagnostic system.

2. Description of the Related Art

Ultrasound diagnostic apparatuses transmit an ultrasound signal (generally having a frequency of 20 kHz or more) to an internal part of an object by using a probe, and obtain an image of the internal part of the object by using information of an echo signal reflected from the object. In particular, the ultrasound diagnostic apparatuses are used for medical purposes such as inspecting the inner area of an object, detecting a foreign material in a body, and assessing an injury. The ultrasound diagnostic apparatuses have a higher stability than diagnostic apparatuses using X-rays, display an image in real time, and are safe because there is no exposure to radioactivity, and thus, may be widely used along with other image diagnostic apparatuses.

An image (hereinafter referred to as an ultrasound image) obtained from an ultrasound diagnostic apparatus may be displayed by the ultrasound diagnostic apparatus, or may be stored in a storage medium and displayed by another image display device. For example, a size of an ultrasound image may be reduced by a portable terminal, a portable electronic device, a personal digital assistant (PDA), a tablet personal computer (PC), or the like, and the ultrasound image may be displayed on a screen.

Ultrasound diagnostic apparatuses may include one or more probes that scan an object. That is, a user of an ultrasound diagnostic apparatus activates one probe, and diagnoses an object by using an ultrasound image obtained from the activated probe.

When additional equipment is mounted on a probe so as to control activation of the probe, the management cost of the probe increases, and moreover, a compatibility problem occurs between various kinds of probes manufactured based on different standards. In addition, when upgrading a probe, an additional cost is incurred for manufacturing and managing additional equipment suitable for a new probe.

SUMMARY

One or more embodiments of the present invention include a probe control method and apparatus for actively activating a probe, used to diagnose an object, among a plurality of probes included in an ultrasound system.

One or more embodiments of the present invention include an ultrasound system including the probe control apparatus.

Additional aspects will be set forth in part in the description which follows and, in part, will be apparent from the description, or may be learned by practice of the presented embodiments.

According to one or more embodiments of the present invention, a probe control apparatus includes: a signal detector that receives identification information of a probe through a cable of the probe, and detects a mounting signal having a predetermined pattern, which is applied to the probe and transferred through the cable, from near a holder with the probe mounted thereon; a sensor that senses a change in a mounting status of the probe recognized with the identification information, on a basis of the detected mounting signal; and a controller that controls the recognized probe to be activated or deactivated according to the change in the mounting status.

The identification information may include information about at least one of a kind and specification of the probe.

The mounting status may be a first status in which the probe is mounted on the holder or a second status in which the probe is separated from the holder.

The mounting signal may be an induced current that is generated by electromagnetic induction and flows through the cable.

A frequency of the mounting signal may be a frequency other than a frequency band used to generate an ultrasound image and a frequency band used to acquire Doppler data.

The signal detector may include a comparator that compares a stored reference signal and the detected mounting signal.

The signal detector may further include: an amplifier that amplifies the detected mounting signal; and a rectifier that rectifies the amplified mounting signal.

The signal detector may detect the mounting signal which is applied during a section between a plurality of ultrasound signals transmitted to an object by the probe.

The probe control apparatus may include a plurality of signal detectors that match a plurality of probes, respectively.

The controller may control the plurality of probes in an order of changed mounting signal or according to predetermined priorities.

The signal detector may be provided at a port in which the cable is connected to the probe control apparatus.

The probe control apparatus may further include a signal transmitter that applies the mounting signal to the probe, wherein the signal transmitter is provided in at least one of the holder, a housing, and a rest on which the probe is mounted.

According to one or more embodiments of the present invention, a probe control method includes: receiving identification information of a probe through a cable of the probe; detecting a mounting signal having a predetermined pattern, which is applied to the probe and transferred through the cable, from near a holder with the probe mounted thereon; sensing a change in a mounting status of the probe recognized with the identification information, on a basis of the detected mounting signal; and controlling the recognized probe to be activated or deactivated according to the change in the mounting status.

According to one or more embodiments of the present invention, an ultrasound diagnostic system comprising the probe control apparatus.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms used in the present invention have been selected as general terms widely used at present, in consideration of the functions of the present invention, but may be altered according to the intent of an operator skilled in the art, conventional practice, or introduction of new technology. Also, if a term is arbitrarily selected by the applicant in a specific case, a meaning of the term in this specific case will be described in detail in a corresponding description portion of the present invention. Therefore, the terms should be defined on the basis of the entire content of this specification instead of a simple name of each of the terms.

In the disclosure below, when it is described that one device comprises (or includes or has) some elements, it should be understood that the device may comprise (or include or has) only those elements, or it may comprise (or include or have) other elements as well as those elements if there is no specific limitation. Moreover, each term such as " . . . unit", " . . . apparatus" and "module" described in specification denotes an element for performing at least one function or operation, and may be implemented via hardware, software, or a combination of hardware and software.

Hereinafter, embodiments of the present invention will be described in detail with reference to the accompanying drawings.

Figure 1:
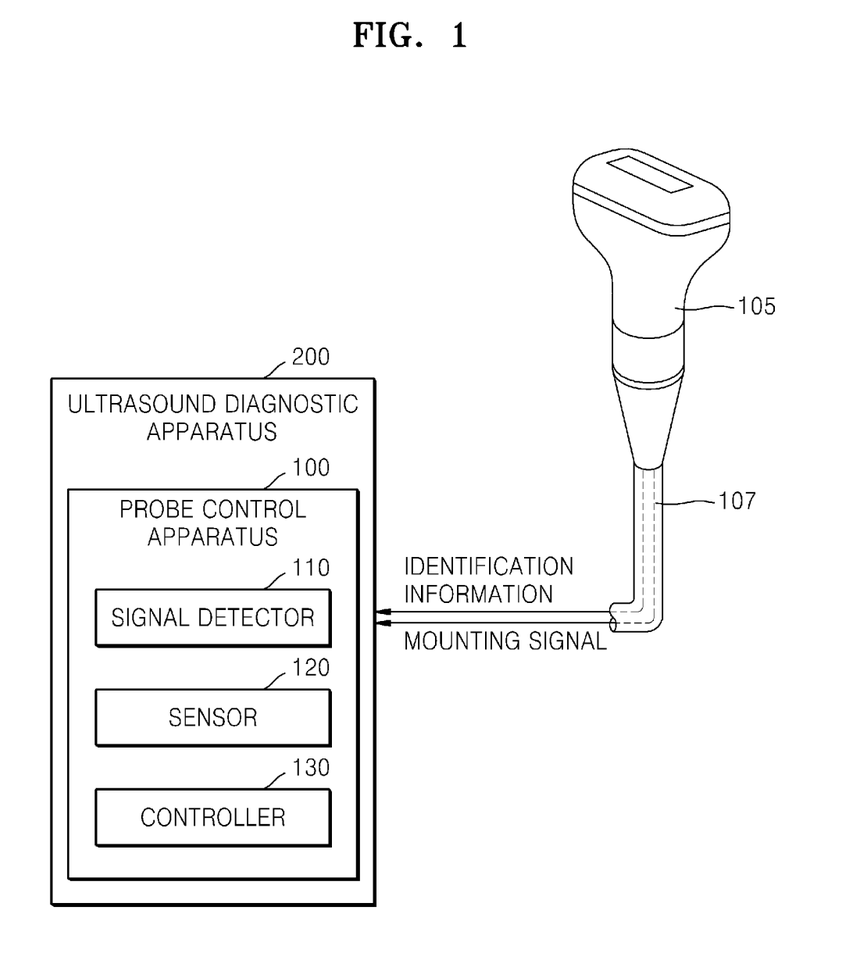
FIG. 1 is a block diagram illustrating a configuration of a probe control apparatus according to an embodiment of the present invention.

FIG. 1 is a block diagram illustrating a configuration of a probe control apparatus 100 according to an embodiment of the present invention. Referring to FIG. 1, the probe control apparatus 100 according to an embodiment of the present invention may include a signal detector 110, a sensor 120, and a controller 130. The probe control apparatus 100 may further include another general-purpose element in addition to the elements of FIG. 1.

The probe control apparatus 100 controls activation or deactivation of one or more probes 105 included in an ultrasound diagnostic apparatus 200. That is, the probe control apparatus 100 may activate a probe 105 which a user desires to use for transmitting an ultrasound signal to an object and receiving an echo signal from the object, or may deactivate a probe 105 which is being used for diagnosing an object.

The ultrasound diagnostic apparatus 200 transmits an ultrasound signal to an object through the probe 105, receives an echo signal from the object, and diagnoses the object by using an ultrasound image generated based on the received echo signal. As illustrated in FIG. 1, the probe control apparatus 100 may be provided in the ultrasound diagnostic apparatus 200. Hereinafter, the elements included in the probe control apparatus 100 will be described in detail.

The signal detector 110 receives identification information through a cable 107 of the probe 105, and detects a mounting signal transferred through the cable 107. The identification information may include information indicating a kind and specification of the probe 105, and for example, may include information about any one kind of a linear array probe, a curvilinear array probe, a convex array probe, and a phased array probe. The identification information may be continuously transferred from the probe 105 to the probe control apparatus 100 through the cable 107, and the signal detector 110 may receive the identification information through the cable 107.

Moreover, the signal detector 110 detects a mounting signal used to determine a mounting status of the probe 105. The signal detector 110 may detect the mounting signal through various methods, and for example, may detect the mounting signal that is an electrical signal received in wired or wireless connection with the cable 107.

Before describing the mounting signal, the mounting status of the probe 105 will be first described. The probe 105 may have two mounting statuses. That is, the mounting status of the probe 105 may be one of a first status in which the probe 105 is mounted on a holder and a second status in which the probe 105 is separated from the holder. In detail, in the first status, the probe 105 may be kept or provided in various kinds of physical equipment such as a holder, a housing, and a rest, and in the second status, when a user of the ultrasound diagnostic apparatus 200 uses the probe 105, the probe 105 may be separated from the equipment by a certain distance or more, and may scan an object.

The mounting signal is a signal indicating whether the mounting status of the probe 105 is the first status or the second status, and may have a predetermined pattern. That is, the mounting signal may be applied to the probe 105, and may be a physical/electrical signal having various predetermined patterns recognizable by the signal detector 110.

According to an embodiment, the mounting signal may be an induced current using electromagnetic induction. That is, the mounting signal is an induced current that is generated by electromagnetic induction caused by a magnetic field changed near the probe 105, and the signal detector 110 may detect an induced current, transferred through the cable 107, as the mounting signal.

In detecting the mounting signal, the signal detector 110 may detect a signal level of the mounting signal. Specifically, the signal detector 110 may detect a signal level of 1 when the mounting signal is transferred through the cable 107, and when the mounting signal is not detected from the cable 107, the signal detector 110 may detect a signal level of 0. An embodiment in which the signal detector 110 detects the signal level of the mounting signal will be described with reference to FIGS. 7A to 7C.

The signal detector 110 may further include various elements for efficiently detecting the mounting signal. According to an embodiment, the signal detector 110 may further include a comparator that compares an intensity of a detected mounting signal with a previously stored reference signal. According to another embodiment, the signal detector 110 may include an amplifier that amplifies a detected mounting signal and a rectifier that rectifies the amplified signal. A detailed embodiment will be described with reference to FIG. 4.

The signal detector 110 may be provided in a port, in which the cable 107 of the probe 105 is connected to the probe control apparatus 100, or in a holder on which the probe 105 is mounted. The embodiment will be described in detail with reference to FIG. 6.

The sensor 120 senses a mounting status of the probe 105 and a change in the mounting status. First, the sensor 120 checks a probe 105 of which a change in a mounting status is intended to be sensed, on the basis of identification information received by the signal detector 110. That is, the sensor 120 may check whether the probe 105, from which the identification information and the mounting signal are received, is a linear array probe or a phased array probe, and determine whether the checked probe 105 is a probe to be activated or deactivated.

Subsequently, the sensor 120 senses a current mounting status of the checked probe 105 (which is checked according to the identification information) and a change in the current mounting status, on the basis of a mounting signal detected by the signal detector 110. For example, the sensor 120 may detect whether a mounting status of the probe 105 is a first status in which the target probe 105 is mounted on a holder or a second status in which the target probe 105 is separated from the holder. Also, the sensor 120 may sense a change from the first status to the second status (or, vice versa).

For example, the sensor 120 may sense a change in a mounting status on the basis of a signal level of the mounting signal detected by the signal detector 110. That is, the sensor 120 may sense the mounting status of the probe 105 as being the first status when the signal level of the mounting signal is detected as being 1, and when a signal level of 0 is detected, the sensor 120 may sense the mounting status of the probe 105 as being the second status. For another example, the sensor 120 may sense the mounting status on the basis of an intensity of the mounting signal. A detailed embodiment in which the sensor 120 senses the mounting status will be described with reference to FIGS. 7A to 7C.

The controller 130 controls an operation of the probe 105 according to the change in the mounting status. That is, the controller 130 performs control in order for one or more probes 105, connected to the ultrasound diagnostic apparatus 200, to be activated or deactivated. When the probe 105 is activated, the probe 105 transmits an ultrasound signal for diagnosing an object, receives an echo signal, and transfers the echo signal to the ultrasound diagnostic apparatus 200. When the probe 105 is deactivated, the probe 105 stops transmission of the ultrasound signal until the probe 105 is again activated.

In controlling a target probe 105, the controller 130 may control the target probe 105 which is checked by the sensor 120 on the basis of identification information received by the signal detector 110. That is, the controller 130 may check a probe which is changed in a mounting status thereof among a plurality of probes connected to the ultrasound diagnostic apparatus 200, and control the checked probe.

When the ultrasound diagnostic apparatus 200 includes a plurality of the probes 150, the controller 130 may perform control to activate or deactivate the plurality of probes 150, on the basis of identification information and a mounting signal which are transferred through the cable 107 of each of the plurality of probes 105. An embodiment of the plurality of probes 105 will be described with reference to FIG. 3.

Figure 2:
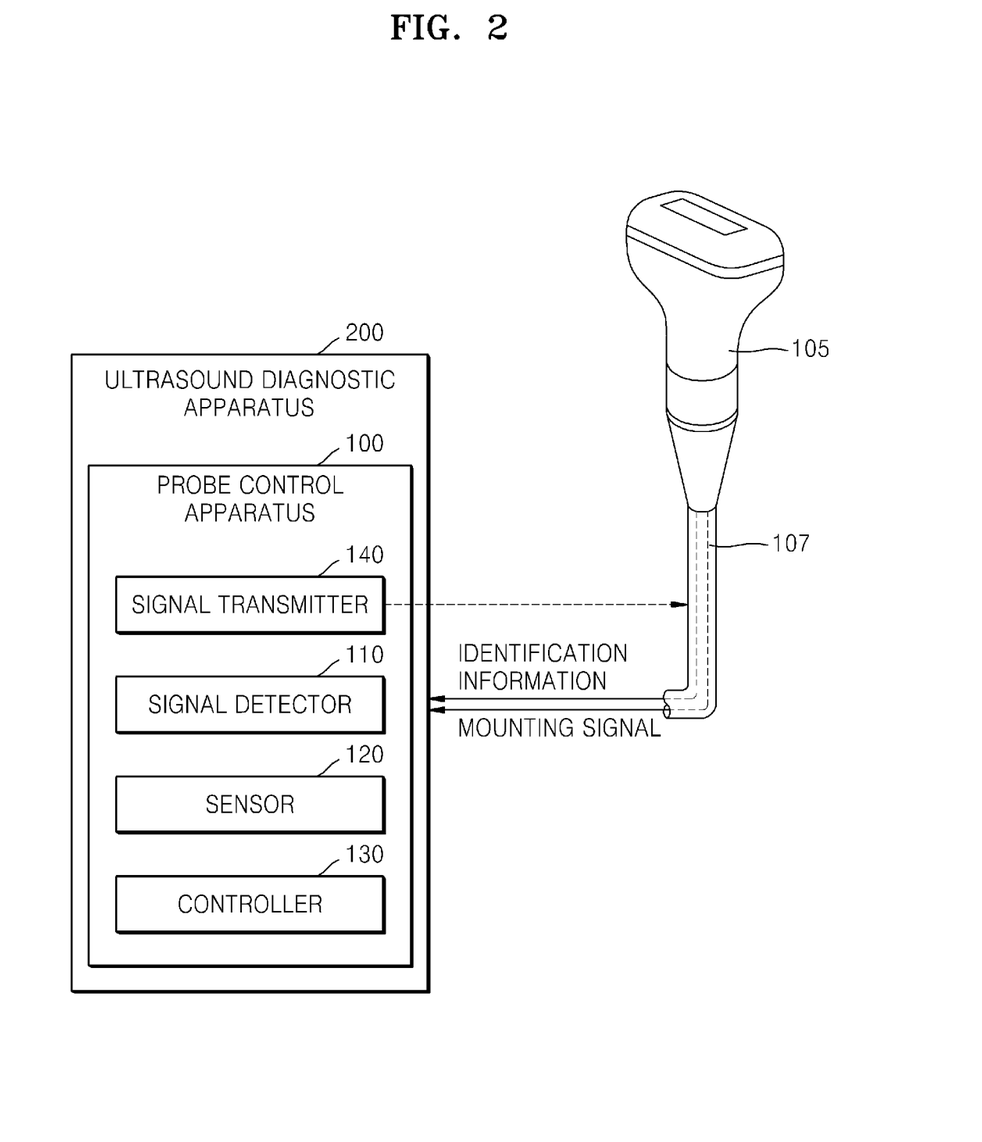
FIG. 2 is a block diagram illustrating a configuration of a probe control apparatus according to another embodiment of the present invention.

FIG. 2 is a block diagram illustrating a configuration of a probe control apparatus 100 according to another embodiment of the present invention. In FIG. 2, in addition to the probe control apparatus 100 described above with reference to FIG. 1, a signal transmitter 140 is illustrated, and a description repetitive of FIG. 1 is not provided.

The signal transmitter 140 applies a mounting signal to the probe 105 or the cable 107 of the probe 105. The mounting signal, as described above, may denote a physical/electrical signal having a predetermined pattern used to sense a mounting status of the probe 105. The mounting signal according to an embodiment may be an induced current generated by electromagnetic induction, and may be a signal having a predetermined pattern.

According to another embodiment, when the signal transmitter 140 applies a mounting signal to the cable 107, a frequency of the mounting signal may be a frequency other than a frequency band used for an ultrasound diagnosis. That is, the signal transmitter 140 may apply a mounting signal, having a frequency other than a frequency band used to generate an ultrasound image and a frequency band used to acquire Doppler data, to the cable 107. Therefore, an influence of the mounting signal is minimized on an operation in which the ultrasound diagnostic apparatus 200 generates and displays an ultrasound image or Doppler image of an object.

For example, a mounting signal may have a frequency other than a frequency band of about 1 kHz to about 44 kHz used to generate an ultrasound image and a frequency band of about 1 MHz to about 25 MHz used to acquire Doppler data. That is, the mounting signal may be a radio frequency (RF) signal having a frequency band between about 44 kHz to 1 MHz or a frequency of 25 MHz or more. The above-described numerical values of the frequency band are merely an example for convenience of description, and the frequency of the mounting signal is not limited to the above-described frequency.

According to another embodiment, the signal transmitter 140 may apply the mounting signal during a section between a plurality of ultrasound signals which are transmitted for diagnosing an object by the probe 105. That is, when the probe 105 repeatedly transmits an ultrasound signal used to generate an ultrasound image, the signal transmitter 140 may apply the mounting signal during the section between the plurality of ultrasound signals, namely, a section in which transmission of the ultrasound signal is transmitted. The embodiment will be described in detail with reference to FIGS. 8A and 8B.

Figure 3:
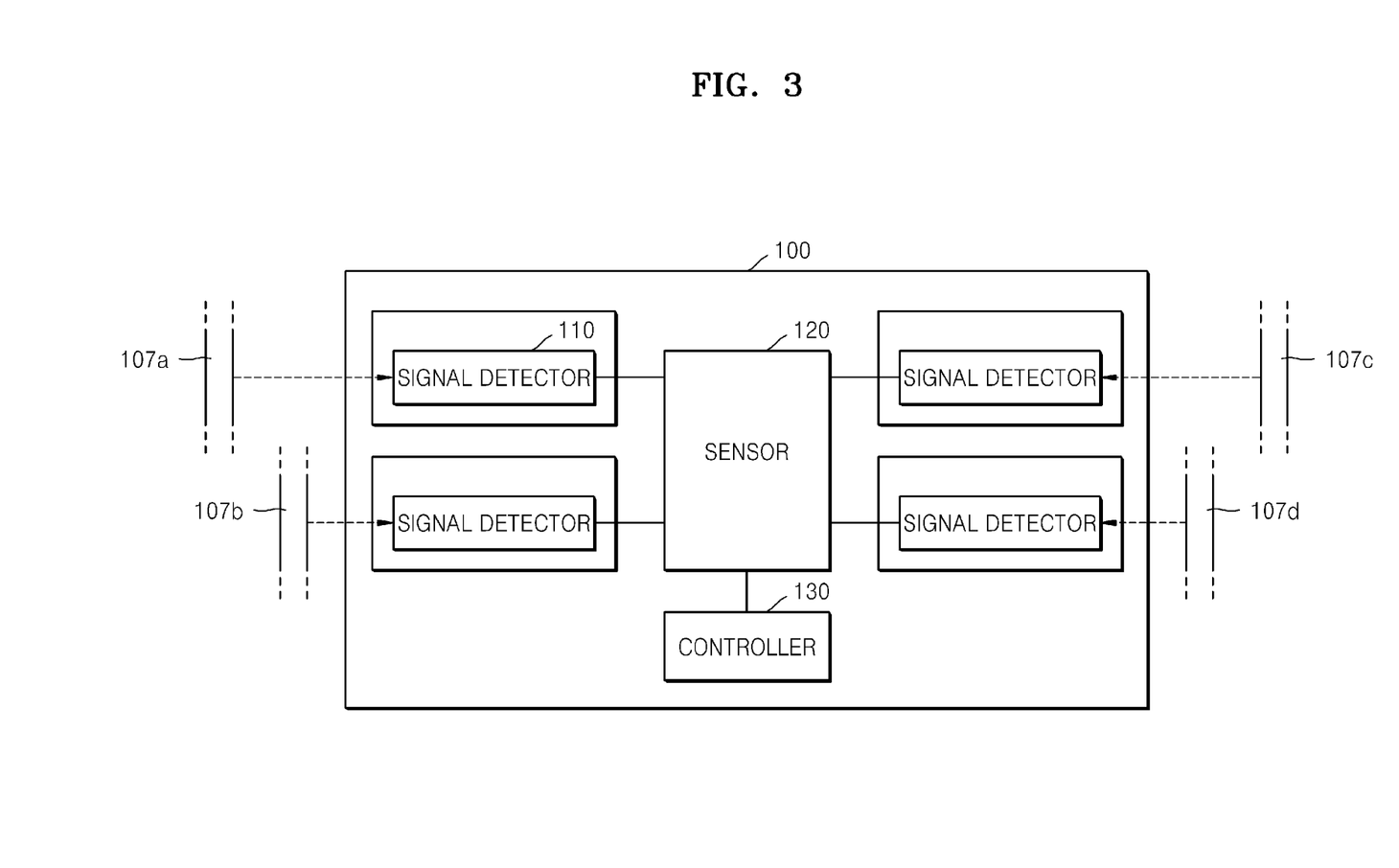
FIG. 3 is a block diagram illustrating a configuration of a probe control apparatus according to another embodiment of the present invention.

FIG. 3 is a block diagram illustrating a configuration of a probe control apparatus 100 according to another embodiment of the present invention. An ultrasound diagnostic apparatus 200 of FIG. 3 may include a plurality of probes 107a to 107d, and the probe control apparatus 100 may be provided inside or outside the ultrasound diagnostic apparatus 200. In FIG. 3, a description repetitive of FIG. 1 is not provided.

The probe control apparatus 100 of FIG. 3 may include a signal detector 110 corresponding to each of the four probes 107a to 107d connected to the ultrasound diagnostic apparatus 200. That is, the probe control apparatus 100 may include the signal detectors 110 equal to the number of probes 107a to 107d such that the signal detectors 110 match the respective probes 107a to 107d.

Therefore, the probe control apparatus 100 may separately sense mounting statuses of the four probes 107a to 107d. That is, the probe control apparatus 100 may sense a mounting status of the first probe 107a on the basis of a first mounting signal which is detected by the signal detector 110 and transferred through a cable of the first probe 107a. Similarly, the probe control apparatus 100 may sense mounting statuses of the second to fourth probes 107b to 107d on the basis of second to fourth mounting signals which are detected by the signal detector 110 and transferred through cables of the second to fourth probes 107b to 107d, respectively.

Subsequently, a controller 130 of the probe control apparatus 100 may separately control and activate/deactivate the four probes 107a to 107d. For example, when the first probe 107a is in a non-mounting status (the second status), that is, it is separated from a holder, the probe control apparatus 100 may activate the first probe 107a, thereby allowing the first probe 107a to transmit an ultrasound signal. Subsequently, when a mounting status of the third probe 107c is changed to the non-mounting status (the second status), the probe control apparatus 100 may activate the third probe 107c, thereby allowing the third probe 107c to transmit an ultrasound signal.

At this time, the probe control apparatus 100 may activate the third probe 107c and simultaneously deactivate the first probe 107a. Alternatively, when a user mounts the first probe 107a on the holder before the mounting status of the third probe 107c is changed to the non-mounting status, the probe control apparatus 100 may deactivate the first probe 107a according to a change in the mounting status of the first probe 107a.

The signal detector 110 simultaneously receives a mounting signal and identification information, and thus, as described above with reference to FIG. 1, a sensor 120 may determine a probe of which a mounting status is changed. Therefore, the controller 130 may control activation/deactivation of the determined target probe. For example, when it is determined based on the received identification information and mounting signal that a mounting status of a convex array probe is changed to the second status when the convex array probe is separated from the holder, the controller 130 may activate the convex array probe.

According to another embodiment, the probe control apparatus 100 may control a plurality of probes in the order of changed mounting statuses or according to predetermined priorities. The embodiment will be described in detail with reference to FIGS. 9A to 9C.

Figure 4:
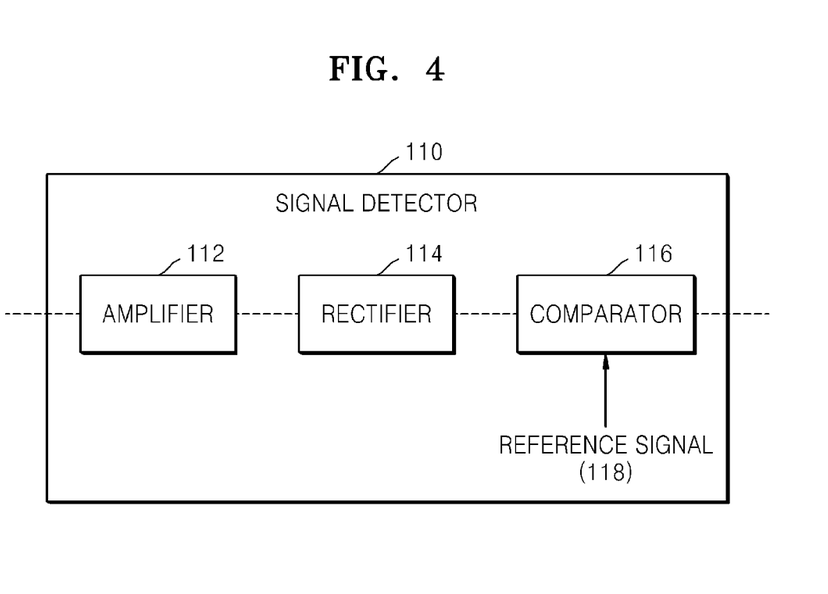
FIG. 4 is a block diagram illustrating a configuration of a signal detector according to an embodiment of the present invention.

FIG. 4 is a block diagram illustrating a configuration of a signal detector 110 according to an embodiment of the present invention. The signal detector 110 according to an embodiment may include at least one of an amplifier 112, a rectifier 114, and a comparator 116.

The amplifier 112 amplifies a mounting signal which is transferred through a cable of a probe. That is, it has been described above that the signal transmitter 140 applies the mounting signal having the frequency other than the frequency band used to generate the ultrasound image or the Doppler data, and thus, an influence of the mounting signal on an ultrasound diagnosis is minimized.

In addition, the signal transmitter 140 may adjust an intensity of the mounting signal in addition to the frequency, thus reducing the influence of the mounting signal on the ultrasound diagnosis. That is, the signal transmitter 140 may apply a mounting signal having a relatively weak intensity compared to various kinds of ultrasound signals, echo signals, and Doppler signals used for the ultrasound diagnosis. The signal transmitter 140 may apply a mounting signal having a predetermined intensity. The amplifier 112 of FIG. 4 may amplify a mounting signal transferred through a cable in order for the mounting signal to be efficiently detected.

The rectifier 114 rectifies the mounting signal, and transfers the rectified mounting signal to the comparator 116. That is, when the mounting signal is an alternating current (AC) current, the rectifier 114 may rectify the mounting signal to convert the mounting signal into a direct current (DC) current. The rectifier 114 may rectify the mounting signal by using a half wave rectifier or a full wave rectifier, and transfer the rectified mounting signal to the comparator 116.

The comparator 116 compares the mounting signal with a stored reference signal 118. For example, the comparator 116 may compare the intensity of the mounting signal with an intensity of the reference signal 118 to determine whether a difference value between the intensities of the two signals is within a certain range. When the difference value between the intensities of the two signals is within the certain range, the comparator 116 may determine the mounting signal, transferred through the cable of the probe, as being successfully detected. On the other hand, when the difference value between the intensities of the two signals is out of the certain range, the comparator 116 may determine the mounting signal as not being detected.

Hereinafter, a method that controls activation or deactivation of a probe by using the elements included in the probe control apparatus 100 will be described in detail with reference to FIG. 5.

Figure 5:
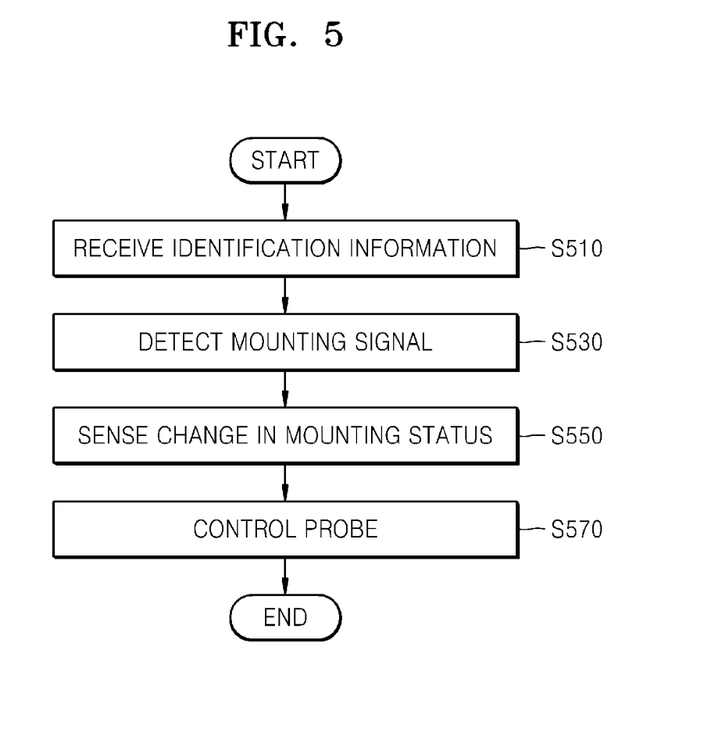
FIG. 5 is a flowchart illustrating a probe control method according to an embodiment of the present invention.

FIG. 5 is a flowchart illustrating a probe control method according to an embodiment of the present invention. In the flowchart of FIG. 5, the method includes a plurality of operations that are sequentially performed in the probe control apparatus 100, the signal transmitter 140, the signal detector 110, the sensor 120, and the controller 130. Therefore, although details are not described below, it can be understood that the above description on the elements of FIGS. 1 to 4 may be applied to the flowchart of FIG. 5.

In operation S510, the probe control apparatus 100 receives identification information of a probe through a cable. The received identification information may include a kind and specification of the probe, and the probe control apparatus 100 may receive the identification information from the probe through a port to which the cable of the probe is connected. The received identification information which is received in operation S510 may be used, along with a mounting signal, for the probe control apparatus 100 to sense a mounting status of the probe.

In operation S530, the probe control apparatus 100 detects the mounting signal transferred through the cable. That is, the probe control apparatus 100 may be connected to the cable in a wired or wireless manner, and may detect the mounting signal. According to an embodiment, the probe control apparatus 100 may amplify and rectify the mounting signal transferred through the cable, and compare the rectified mounting signal with a predetermined reference signal, thereby efficiently detecting the mounting signal. The mounting signal which is detected in operation S530 may be detected by the signal detector 110 which is provided near the port to which the ultrasound diagnostic apparatus 200 and the cable are connected.

The mounting signal may be an induced current generated by electromagnetic induction as described above with reference to FIG. 1, and may be a physical/electrical signal having a predetermined pattern. The probe control apparatus 100 may detect the mounting signal on the basis of a received signal and the predetermined pattern.

The mounting signal which is detected in operation S530, although not shown in FIG. 5, may be applied by the signal transmitter of the probe control apparatus 100. That is, the probe control apparatus 100 may apply the mounting signal to the probe or the cable of the probe, near a holder, a rest, and a housing on which the probe is mounted. Also, the mounting signal may be a signal having a frequency other than a frequency band used for an ultrasound diagnosis, and may be applied during a section between a plurality of repeated ultrasound signals.

In operation S550, the probe control apparatus 100 checks a current mounting status, and senses a change in the mounting status of the probe. That is, the probe control apparatus 100 may determine whether the probe checked with the identification information is in the first status in which the probe is mounted on the holder or the second status separated from the holder for diagnosing an object, on the basis of the mounting signal. Further, the probe control apparatus 100 may sense that the mounting status is changed from the first status to the second status, according to an intensity change of the mounting signal.

In operation S570, the probe control apparatus 100 actively controls the probe according to a change in the mounting status. That is, when a probe separated from the holder for diagnosing the object is sensed in operation S550, the probe control apparatus 100 may control the sensed probe to be activated. On the other hand, when use of the probe control apparatus 100 is ended and a probed mounted on the holder is sensed, the probe control apparatus 100 may control the sensed probe to be deactivated.

Therefore, although separate additional equipment is mounted on the probe included in the ultrasound diagnostic apparatus 200, the probe control apparatus 100 may automatically activate/deactivate the probe, and actively control the probe. Also, a user of the ultrasound diagnostic apparatus 200 and probe control apparatus 100 may not perform unnecessary manipulation, such as selecting a probe desiring to activate a user interface, each time a probe for diagnosing the object is changed.

Figure 6:
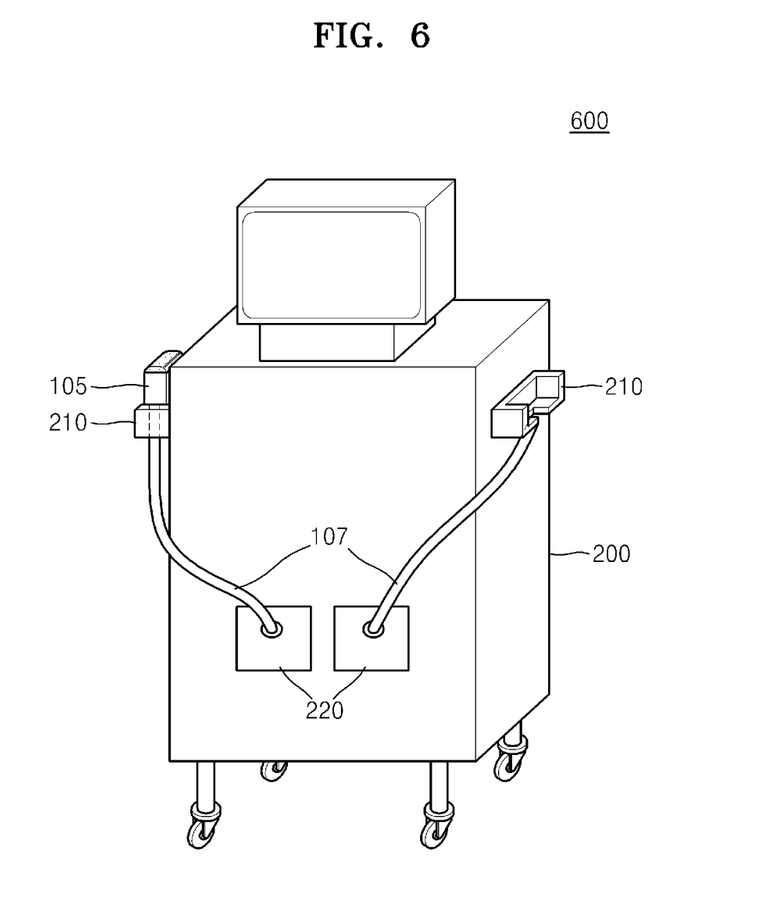
FIG. 6 is a diagram illustrating an ultrasound diagnostic system including a probe control apparatus according to an embodiment of the present invention.

FIG. 6 is a diagram illustrating an ultrasound diagnostic system including the probe control apparatus 100 according to an embodiment of the present invention. The ultrasound diagnostic system 500 of FIG. 6 may include the ultrasound diagnostic apparatus 200 with the probe control apparatus 100 provided therein, one or more probes 105, and a cable 107 connected to each of the probes 105.

In the ultrasound diagnostic system 500 of FIG. 6, the probe 105 may be mounted on the holder 210, and a space through which the cable 107 passes may be provided at a bottom of a holder 210. A type of the holder 210 illustrated in FIG. 6 is merely a simple example, and the probe 105 may be kept in different members such as a housing and a rest, in addition to the holder 210. The cable 107 of the probe 105 is connected to the ultrasound diagnostic apparatus 200 through a port 220 which is provided at the ultrasound diagnostic apparatus 200.

The signal transmitter 140 and signal detector 110 of the probe control apparatus 100 may be respectively provided at different positions in the holder 210 or port 220 of the ultrasound diagnostic apparatus 200. That is, when the signal transmitter 140 according to an embodiment is provided near the holder 210, the signal detector 110 may be provided near the port 220, and a case opposite thereto may be considered.

For example, to provide a detailed description on an embodiment in which the signal transmitter 140 or the signal detector 110 is provided near the holder 210, the signal transmitter 140 or the signal detector 110 may be provided at the bottom of the holder 210 or at a side surface of the ultrasound diagnostic apparatus 200 with the holder 210 adhered thereto. That is, the signal transmitter 140 or the signal detector 110 may be provided at a position which is sufficiently close to apply a mounting signal to the cable 107 of the probe near the holder 210.

According to another embodiment, the signal transmitter 140 or the signal detector 110 may be provided near the port 220. That is, the signal transmitter 140 or the signal detector 110 may be provided at various positions which enable a connection of the cable 107 such as a signal pin, a ground pin, or a power pin, or a PSA pin of the port 220 of the ultrasound diagnostic apparatus 200.

Figure 7A:
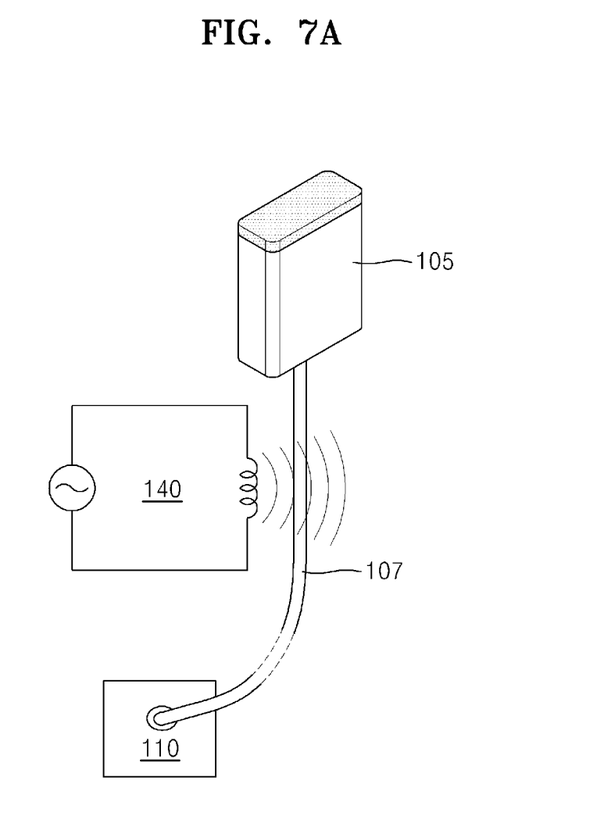
FIGS. 7A to 7C are diagrams for describing an operation of a probe control apparatus according to an embodiment of the present invention.
Figure 7B:
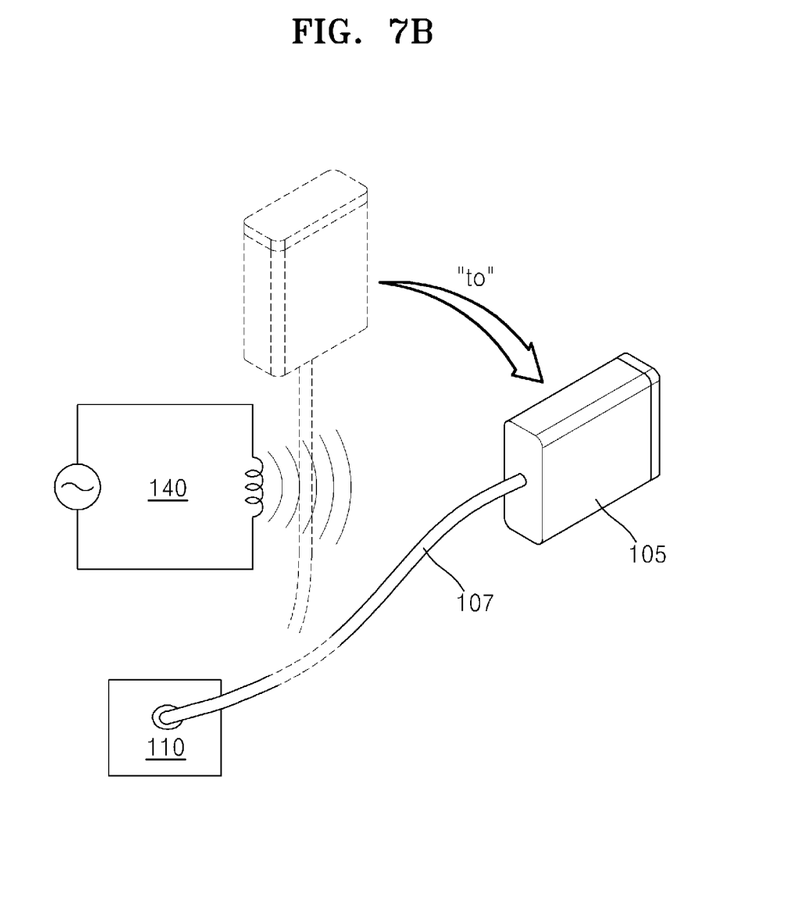
Figure 7C:
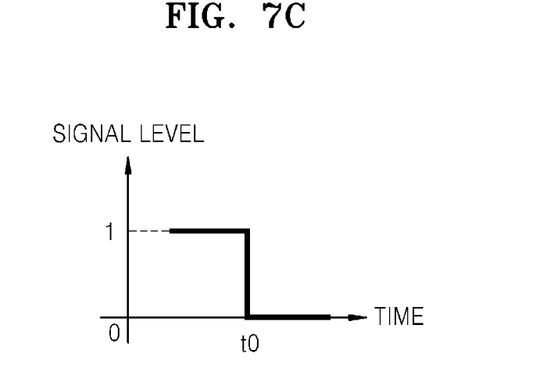

FIGS. 7A to 7C are diagrams for describing an operation of the probe control apparatus 100 according to an embodiment of the present invention. FIGS. 7A to 7C are diagrams for describing an operation in which the probe control apparatus 100 receives identification information, detects a mounting signal, and senses a change in a mounting status of the probe 105.

In FIG. 7A, the probe 105 is in the first status in which the probe 105 is kept in the holder, the housing, or the rest. The signal transmitter 140 of the probe control apparatus 100 applies a mounting signal to the cable 107 of the probe 105, and the signal detector 110 detects the mounting signal that is an induced current transferred through the cable 107.

When the cable 107 is an optical cable that converts an electrical signal into a ray signal, the signal transmitter 140 may not directly apply the mounting signal to the cable 107 but may apply the mounting signal to a head portion of the probe 105. The probe 105 may analog-digital-convert the applied mounting signal to transmit the digital-converted mounting signal to the cable 107, and the signal detector 110 may detect the digital-converted mounting signal.

In FIG. 7B, in order to diagnose an object by using the probe 105 of which a mounting status is the first status, a user of the ultrasound diagnostic apparatus 200 separates the probe 105 from the rest. A time, at which the probe 105 is separated from the holder (the second status) and thus the mounting signal is not applied to the cable 107, is referred to as t0.

FIG. 7C illustrates changing of the mounting status of the probe 105 from the first status to the second status at the time t0, that is, changing of a signal level of a detected mounting signal. That is, before the time t0, the probe control apparatus 100 detects a mounting signal having a signal level of 1 transferred through the cable 107. When the probe 105 is separated from the holder at the time t0, the cable 107 is separated up to a position corresponding to a distance which is not sufficient for the signal transmitter 140 to apply the mounting signal. Therefore, the signal level of the detected mounting signal is shown as 0.

The signal detector 110 continuously receives identification information of the probe 105, separately from a change in the signal level of the mounting signal illustrated in FIGS. 7A to 7C. That is, the signal detector 110 may continuously receive the identification information of the probe 105 through the cable, separately from that the signal level of the mounting signal is changed according to a change in a distance between the signal transmitter 140 and the cable 107. Therefore, when the level of the mounting signal of the probe 105 determined based on the identification information is changed, the probe control apparatus 100 may activate or deactivate a corresponding probe.

When a mounting signal sensed before the time t0 is not sensed after the time t0, the probe control apparatus 100 determines that the mounting status of the probe 105 is changed, and automatically activates the probe 105. That is, the probe control apparatus 100 determines that the user desires to diagnose an object by using the probe 105, and automatically activates the probe 105 determined based on the identification information so as to transmit an ultrasound signal.

Unlike the embodiments of FIGS. 7A to 7C, when an activated probe 105 is again mounted on the holder and a status thereof is changed to the first status (the mounting status), the probe control apparatus 100 may detect a mounting signal having a signal level of 1. Therefore, the probe control apparatus 100 may automatically deactivate a target probe 105 determined based on identification information.

Figure 8A:
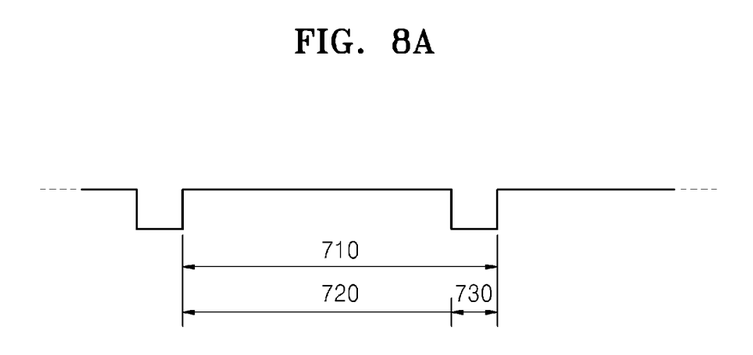
FIGS. 8A and 8B are diagrams for describing a time section in which a mounting signal is applied, according to an embodiment of the present invention.
Figure 8B:
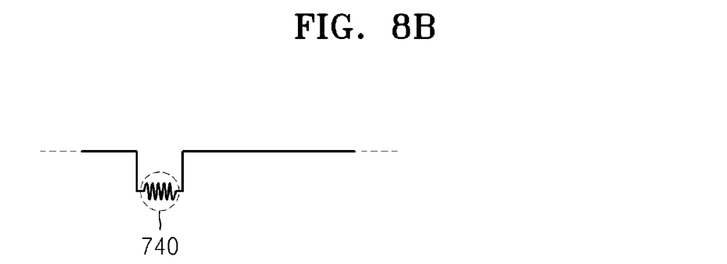

FIGS. 8A and 8B are diagrams for describing a time section in which a mounting signal is applied, according to an embodiment of the present invention. FIG. 8A shows a plurality of ultrasound signals which are transmitted to an object by a probe. FIG. 8B shows a mounting signal applied by the probe control apparatus 100.

The probe transmits a plurality of ultrasound signals (118, 256, or more), and receives an echo signal to generate an ultrasound image corresponding to one frame. That is, the probe focuses and transmits a plurality of ultrasound signals, for generating an ultrasound image.

In FIG. 8A, a section 710 shows a one-time ultrasound signal transmitted by the probe. That is, the probe transmits the ultrasound signal during a section 720, stops transmission of the ultrasound signal during a section 730, and transmits an ultrasound signal used to form a scan line after the section 730.

In FIG. 8B, the probe control apparatus 100 may apply a mounting signal during a section 740 that is a section between a plurality of ultrasound signals transmitted by the probe. That is, the probe control apparatus 100 may be synchronized with a clock of the ultrasound diagnostic apparatus 200 and probe, and may apply the mounting signal during the section 740 in which the probe stops transmission of the ultrasound signal.

When a mounting status of the probe is the first status in which the probe is mounted on the holder, the probe does not transmit an ultrasound signal, and thus, the probe control apparatus 100 may apply a mounting signal to a cable irrespective of the probe. On the other hand, when the probe is activated and transmit an ultrasound signal, the probe control apparatus 100 may apply a mounting signal during a section between a plurality of repeated ultrasound signals. Therefore, the probe control apparatus 100 minimizes an influence of the mounting signal on the ultrasound signal transmitted by the probe.

Figure 9A:
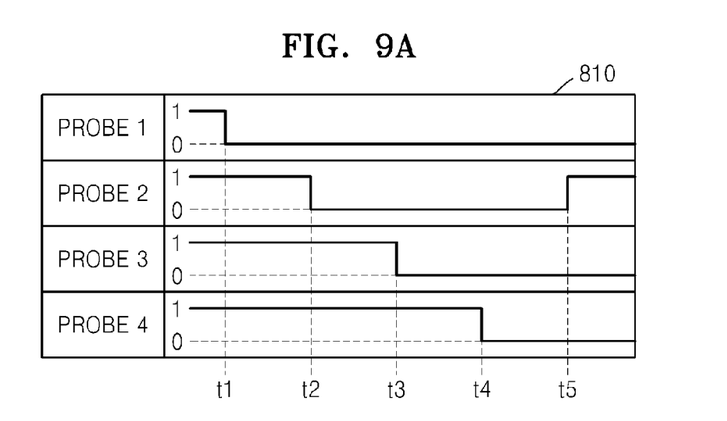
FIGS. 9A to 9C are diagrams for describing an example of controlling a plurality of probes.
Figure 9B:
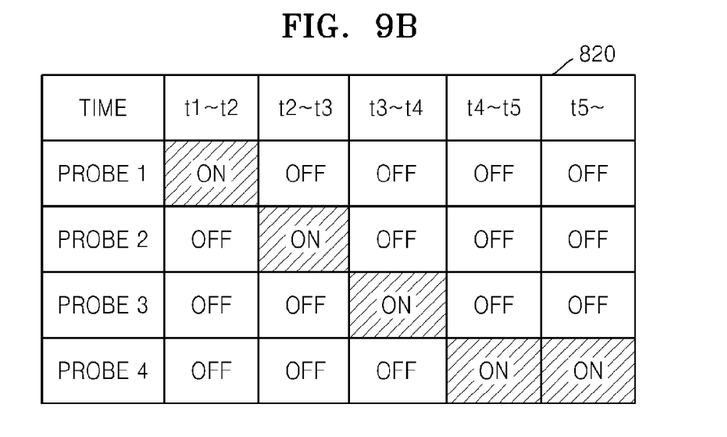
Figure 9C:
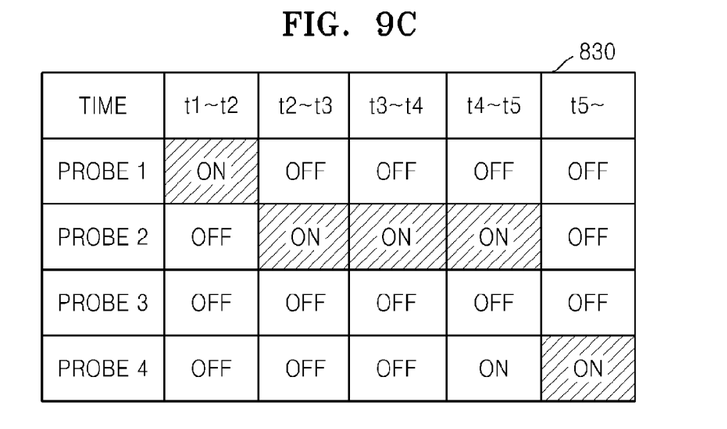

FIGS. 9A to 9C show shows diagrams for describing an example of controlling a plurality of probes according to embodiments of the present invention. FIGS. 9A to 9C show tables 810, 820, and 830 for describing two embodiments in which the probe control apparatus 100 controls a plurality of probes.

First, the table 810 shows four probes which are sequentially activated. That is, before a time t1, the probe control apparatus 100 detects from among all probes 1 to 4 a mounting signal having a signal level 1. That is, the probes 1 to 4 are in the first status (a mounting status) in which the probes 1 to 4 are mounted on the respective holders.

At the time t1, the probe control apparatus 100 senses a change in a mounting signal of the probe 1. That is, the probe 1 is separated from a corresponding holder, and thus, a signal level of the mounting signal of the probe 1 is changed to 0. Subsequently, the respective mounting signals of the probes 2 to 4 are sequentially changed at times t2, t3 and t4. That is, the probes 2 to 4 are also separated from the respective holders.

Finally, at a time t5, the probe control apparatus 100 senses a change in the mounting signal of the probe 2. That is, the probe control apparatus 100 senses that a signal level of the mounting signal of the probe 2 is changed to 1. The change in the mounting signal of the probe 2 may denote that a user ends the use of the probe 2 and then keeps the probe 2 in a corresponding holder.

The table 820 is for describing an embodiment in which the probe control apparatus 100 controls the four probes 1 to 4 in the order of changed mounting signal. That is, the probe control apparatus 100 senses a change of the mounting signal of the probe 1 at the time t1, and controls and activates the probe 1.

Subsequently, the signal levels of the respective mounting signals of the probes 2 to 4 are respectively changed at the times t2, t3 and t4, and thus, the probe control apparatus 100 sequentially activates the probes 2 to 4. For example, the probe control apparatus 100 may deactivate the probe 1 (which was deactivated during an interval from the time t1 to the time t2) while activating the probe 2 at the time t2.

The table 830 is for describing an embodiment in which the probe control apparatus 100 controls the four probes 1 to 4 according to predetermined priorities. The table 830 presents an embodiment in which the probe 2 is activated prior to the probes 1, 3, and 4. Details before the time t3 are the same as those in the table 820.

At the time t3, a change in the mounting signal of the probe 3 is sensed, but since the probe 2 is prior to the other probes, the probe control apparatus 100 performs control to continuously activate the probe 2. Similarly, even at the time t4, although the probe control apparatus 100 senses a change in the mounting signal of the probe 4, the probe control apparatus 100 may activate the probe 2.

At the time t5, a signal level of the probe 2 that is a probe having a priority is sensed as 1. That is, when the use of the probe is ended, the probe control apparatus 100 may perform control to activate the probes 1, 3 and 4 other than the probe 2 having the priority.

For example, the probe control apparatus 100 may control the probes 1, 3 and 4 according to priorities thereof. That is, the use of the probe 2 having the foremost priority is ended, the probe control apparatus 100 may control the other probes according to subsequent priorities. On the other hand, when only the probe 2 has a foremost priority and the other probes have the same priority, the probe control apparatus 100 may control the other probes in the order of changed mounting statuses.

That is, after the time t5 of the table 830, the probe control apparatus 100 may activate the probe 4 of which the mounting status is finally changed to the second status, except the probe 2. The above-described priorities listed in the table 830 may be previously stored in the probe control apparatus 100 according to selection of the user, and changed in the middle of diagnosing an object.

The probe control apparatus and method and the ultrasound system automatically activate/deactivate the probe even without additional equipment being mounted on the probe, and thus actively control the probe. That is, by using the cable of the probe as an antenna, a motion of the probe is automatically sensed and controlled.

Moreover, a user of the ultrasound diagnostic apparatus 200 and probe control apparatus 100 may not perform unnecessary manipulation, such as selecting a probe in order to activate a user interface each time a probe for diagnosing the object is changed.

In addition, the probe control apparatus and method and the ultrasound system are free of any compatibility problems between various kinds of probes, and moreover enhance a performance of the probe, thereby preventing inconvenience when upgrade of a device is necessary. Also, when a problem occurs in the probe control apparatus and the ultrasound system, the probe control apparatus and the ultrasound system may be repaired separately from the probe. Accordingly, the cost for manufacturing and maintaining peripheral equipment of the ultrasound system is reduced, and an inconvenience problem is solved.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A probe control apparatus comprising:
a signal transmitter that causes an induced current to flow in at least one of a probe or a cable of the probe by generating a magnetic field;
a signal detector that receives identification information of the probe through the cable of the probe, and detects a mounting signal which is the induced current generated by electromagnetic induction and transferred through the cable, wherein a level of the detected mounting signal changes according to a distance between the signal transmitter and the cable of the probe;
a sensor that senses a change in a mounting status of the probe recognized with the identification information, on a basis of the level of the detected mounting signal; and
a controller that controls the recognized probe to be activated or deactivated according to the change in the mounting status.

2. The probe control apparatus of claim 1, wherein the identification information includes information about at least one of a kind or specification of the probe.

3. The probe control apparatus of claim 1, wherein the mounting status is a first status in which the probe is mounted on the holder or a second status in which the probe is separated from the holder.

4. The probe control apparatus of claim 1, wherein a frequency of the mounting signal is a frequency other than a frequency band used to generate an ultrasound image and a frequency band used to acquire Doppler data.

5. The probe control apparatus of claim 1, wherein the signal detector includes a comparator that compares a stored reference signal and the detected mounting signal.

6. The probe control apparatus of claim 5, wherein the signal detector further includes:

an amplifier that amplifies the detected mounting signal; and
a rectifier that rectifies the amplified mounting signal.

7. The probe control apparatus of claim 1, wherein the signal detector detects the mounting signal which is applied during a section between a plurality of ultrasound signals transmitted to an object by the probe.

8. The probe control apparatus of claim 1, comprising a plurality of signal detectors that match a plurality of probes, respectively.

9. The probe control apparatus of claim 8, wherein the controller controls the plurality of probes in an order of changed mounting signals or according to predetermined priorities.

10. The probe control apparatus of claim 1, wherein the signal detector is provided at a port in which the cable is connected to the probe control apparatus.

11. The probe control apparatus of claim 1, wherein the signal transmitter is provided in at least one of the holder, a housing, or a rest on which the probe is mounted.

12. An ultrasound diagnostic system comprising the probe control apparatus of claim 1.

13. A probe control method comprising:
causing, by a signal transmitter, an induced current to flow in at least one of a probe or a cable of the probe by generating a magnetic field;
receiving identification information of the probe through the cable of the probe;
detecting a mounting signal which is the induced current generated by electromagnetic induction and transferred through the cable, wherein a level of the detected mounting signal changes according to a distance between the signal transmitter and the cable of the probe;
sensing a change in a mounting status of the probe recognized with the identification information, on a basis of the level of the detected mounting signal; and
controlling the recognized probe to be activated or deactivated according to the change in the mounting status.

14. The probe control method of claim 13, wherein the identification information includes information about at least one of a kind or specification of the probe.

15. The probe control method of claim 13, wherein the mounting status is a first status in which the probe is mounted on the holder or a second status in which the probe is separated from the holder.

16. The probe control method of claim 13, wherein a frequency of the mounting signal is a frequency other than a frequency band used to generate an ultrasound image and a frequency band used to acquire Doppler data.

17. The probe control method of claim 13, wherein the detecting includes comparing a stored reference signal and the detected mounting signal.

18. The probe control method of claim 17, further comprising:
amplifying the detected mounting signal; and
rectifying the amplified mounting signal.

19. The probe control method of claim 13, wherein the detecting includes detecting the mounting signal which is applied during a section between a plurality of ultrasound signals transmitted to an object by the probe.

20. The probe control method of claim 13, wherein the receiving and the detecting are performed by each of a plurality of probes.

21. The probe control method of claim 20, wherein the controlling includes controlling the plurality of probes in an order of changed mounting signal or according to predetermined priorities.

22. The probe control method of claim 13, wherein the receiving and the detecting are performed at a port in which the cable is connected to the probe control apparatus.

23. The probe control method of claim 13, wherein the causing is performed in at least one of the holder, a housing, or a rest on which the probe is mounted.

* * * * *